United States Patent
Jeon et al.

(10) Patent No.: US 6,905,500 B2
(45) Date of Patent: Jun. 14, 2005

(54) BONE FIXATION APPARATUS

(75) Inventors: Chang-Hun Jeon, Seoul (KR); Howard S. An, Chicago, IL (US); Ja-Kyo Koo, Seoul (KR)

(73) Assignee: U & I Corporation, Kyunggi-do (KR)

( * ) Notice: Subject to any disclaimer, the term of this patent is extended or adjusted under 35 U.S.C. 154(b) by 9 days.

(21) Appl. No.: 10/296,609

(22) PCT Filed: Feb. 4, 2002

(86) PCT No.: PCT/KR02/00159
§ 371 (c)(1),
(2), (4) Date: Nov. 21, 2002

(87) PCT Pub. No.: WO03/037199
PCT Pub. Date: May 8, 2003

(65) Prior Publication Data
US 2003/0158552 A1 Aug. 21, 2003

(30) Foreign Application Priority Data
Oct. 31, 2001 (KR) ....................... 2001-67394

(51) Int. Cl.[7] ............................................. A61B 17/56
(52) U.S. Cl. ........................................ 606/61; 606/73
(58) Field of Search ............................. 606/60, 61, 73, 606/72; 411/308–311, 380, 381, 396, 436

(56) References Cited

U.S. PATENT DOCUMENTS

| | | | | |
|---|---|---|---|---|
| 1,328,600 A | * | 1/1920 | Smith | 403/137 |
| 1,428,715 A | * | 9/1922 | Shaw | 403/135 |
| 3,352,342 A | * | 11/1967 | Jacobson | 411/282 |
| 3,483,888 A | * | 12/1969 | Wurzel | 137/539 |
| 3,896,867 A | * | 7/1975 | Gill et al. | 411/353 |
| 4,319,756 A | * | 3/1982 | Brown | 277/507 |
| 4,628,920 A | * | 12/1986 | Mathys et al. | 606/62 |
| 4,840,526 A | * | 6/1989 | Bourdonne | 411/263 |
| 5,127,175 A | * | 7/1992 | Atkinson | 37/270 |
| 5,207,678 A | | 5/1993 | Harms et al. | |
| 5,443,467 A | * | 8/1995 | Biedermann et al. | 606/65 |
| 5,476,464 A | | 12/1995 | Metz-Stavenhagen et al. | |
| 5,554,157 A | | 9/1996 | Errico et al. | |
| 5,865,581 A | * | 2/1999 | Sadri et al. | 411/5 |
| 6,063,090 A | * | 5/2000 | Schlapfer | 606/61 |
| 6,280,442 B1 | | 8/2001 | Barker et al. | |
| 6,565,567 B1 | * | 5/2003 | Haider | 606/61 |
| 6,648,888 B1 | * | 11/2003 | Shluzas | 606/61 |
| 6,733,502 B2 | * | 5/2004 | Altarac et al. | 606/61 |
| 2001/0026746 A1 | * | 10/2001 | Calandra et al. | 411/436 |
| 2003/0103832 A1 | * | 6/2003 | Cords et al. | 411/308 |

OTHER PUBLICATIONS

Abstract of Korean Patent 2000–048562. "Multi–Axial Bone Screw Assembly". Mar. 9, 1999.

* cited by examiner

*Primary Examiner*—Pedro Philogene
*Assistant Examiner*—David A Bonderer
(74) *Attorney, Agent, or Firm*—Merchant & Gould P.C.

(57) ABSTRACT

Disclosed is a bone fixation apparatus. This device comprises a bone screw having a head; a cap member placed on an upper part of the head of the bone screw; a receiver member having a bore in which the cap member and the head of the bone screw are respectively accommodated and held, and a U-shaped channel through which a support bar extends; and a compression member threadedly coupled into the receiver member to downwardly bias the support bar. A multitude of stepped portions are formed at a lower end and inner surface of the receiver member to be brought into linear contact with an outer surface of a lower part of the head so that the supporting force for the head of the bone screw is increased.

7 Claims, 8 Drawing Sheets

Prior Art

Prior Art

BONE FIXATION APPARATUS

FIELD OF THE INVENTION

The present invention relates to a bone fixation apparatus which is used for fixing and stabilizing a bone such as the spine, and so forth, after the bone is corrected into its normal state.

BACKGROUND OF THE INVENTION

Various bone fixation apparatuses have been disclosed in the art, such as those described in Korean Patent Laid-open Publication No. 2000-48562 and U.S. Pat. No. 6,280,442.

As shown in FIG. 1, the bone fixation apparatus described in Korean Patent Laid-open Publication No. 2000-48562 includes a bone screw 10, a shrinkage collet 14, a receiver member 18, and a set screw 20. The bone screw 10 has a spherical head 12. The shrinkage collet 14 functions to support the head 12 of the bone screw 10. The receiver member 18 has a center bore for delimiting a tapered recess 16 in which the shrinkage collet 14 is accommodated and a U-shaped channel that communicates with the recess 16 and through which a support bar R extends. The setscrew 20 is threadedly coupled to the receiver member 18 to downwardly bias the support bar R.

The head 12 of the bone screw 10 is defined with a tool-engaging groove 22 in which a tool can be engaged. The tool engaging groove 22 is defined on a flat upper end surface 24 of the head 12, in which the upper end surface 24 is formed by truncating the head 12. A portion of the receiver member 18 which defines the U-shaped channel is formed with internal threads 26 so that the setscrew 20 can be threadedly coupled to the internal threads 26. A lower surface of the shrinkage collet 14 is formed to have a contoured depression 28 in which the head 12 is partially accommodated. In the contoured depression 28, a lower part of the shrinkage collet 14 is formed with a plurality of slots, so that a desired pressing force is applied to the head 12 of the bone screw 10.

If the setscrew 20 is tightened, the support bar R compresses the shrinkage collet 14, and the shrinkage collet 14 is squeezed within the tapered recess 16 of the receiver member 18 in such a way as to fixedly hold the bone screw 10 at a vertical or inclined position.

Meanwhile, as shown in FIG. 2, in the bone fixation apparatus described in U.S. Pat. No. 6,280,442, a series of ridges 34 are formed on a head 32 of a bone screw 30, a retainer ring 38 is fitted adjacent to a lower end of a receiver member 36 so that the head 32 can be retained by the retainer ring 38. A cap member 40 is placed on an upper part of the head 32. Above the cap member 40, a support bar R is inserted through a U-shaped channel defined in the receiver member 36 and then biased downward by a compression member 42.

In the receiver member 36, a lower part in which the cap member 40 is inserted is formed to have an inner diameter greater than that of the upper part into which the compression member 42 is threadedly coupled. Due to this fact, even in the case that the compression member 42 is unscrewed and the support bar R is removed, the cap member 40 is prevented from being released in an upward direction. When assembling the bone fixation apparatus, after the cap member 40 and the head 32 of the bone screw 30 are sequentially inserted through the lower end of the receiver member 36, the retainer ring 38 is placed around and moved upward on the bone screw 30 and then fitted into an inward annular groove defined adjacent to the lower end of the receiver member 36.

The internal threads of the receiver member 36 may be formed in a manner such that the cap member 40 is also threadedly coupled to the internal threads to be prevented from being released from the receiver member 36.

However, in the former bone fixation apparatus as described in Korean Patent Laid-open Publication No. 2000-48562, the head 12 supported in the tapered recess 16 is likely to be moved by an external factor because the supporting force is insufficient. Consequently, the head 12 cannot be reliably maintained in an initially supported state.

The latter type bone fixation apparatus as described in U.S. Pat. No. 6,280,442, while coping to some extent the problem caused in Korean Patent Laid-open Publication No. 2000-48562, suffers from defects in that it is difficult to fit the retainer ring 38 in place, and the supporting force of the bone screw is still insufficient.

When the head of the bone screw is supported by the cap member threadedly coupled to the receiver member, it is not easy to screw the cap member adjacent to the lower end of the receiver member. Further, because the biasing force of the compression member cannot be transferred to the head, assemblability is deteriorated and the supporting force of the bone screw is downgraded.

SUMMARY OF THE INVENTION

The present invention provides a bone fixation apparatus with an improved supporting force of a bone screw, thereby preventing movement of a bone, and at the same time, is assembled in an easy manner.

According to an embodiment of the present invention, there is provided a bone fixation apparatus comprising: a bone screw having a head; a cap member placed on an upper part of the head of the bone screw; a receiver member having a bore in which the cap member and the head of the bone screw are respectively accommodated and held and a U-shaped channel through which a support bar extends; and a compression member threadedly coupled into the receiver member to downwardly bias the support bar; wherein a multitude of stepped portions are formed at a lower end of and on an inner surface of the receiver member to be brought into linear contact with an outer surface of a lower part of the head so that the supporting force for the head of the bone screw is increased.

According to another embodiment of the present invention, a recess with a certain depth is defined on a lower surface of the cap member, and at a lower end of the recess, the cap member is brought into linear contact with an outer surface of the upper part of the head.

According to another embodiment of the present invention, the bore is formed therein with a multitude of stepped portions, an accommodating chamber defined above the stepped portions to accommodate the cap member, and internal threads on which the cap member is threadedly moved and to which the compression member is threadedly coupled, the accommodating chamber having an inner diameter greater than that of the internal threads.

According to another embodiment of the present invention, an upper portion of the internal threads has a thread height greater than that of the lower portion of the internal threads, so that the cap member can be threadedly moved on both of the upper and lower portions of the internal threads and the compression member can be threadedly moved only on the upper portion and cannot be threadedly moved on the lower portion of the internal threads.

According to another embodiment of the present invention, the internal threads comprise trapezoidal threads, so that deformation of the receiver member can be prevented and the internal threads can provide optimized results in terms of force transfer, locking efficiency, and prevention of unscrewing.

According to still another embodiment of the present invention, the trapezoidal thread has an upper surface which is formed to have a slope greater than that of the lower surface, so that the cap member and the compression member can be easily assembled while preventing the cap member from being unintentionally unscrewed.

According to yet still another embodiment of the present invention, the upper and lower surfaces of the trapezoidal thread have slopes of 10° and 1°, respectively.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF PREFERRED EMBODIMENTS

Figure 1:
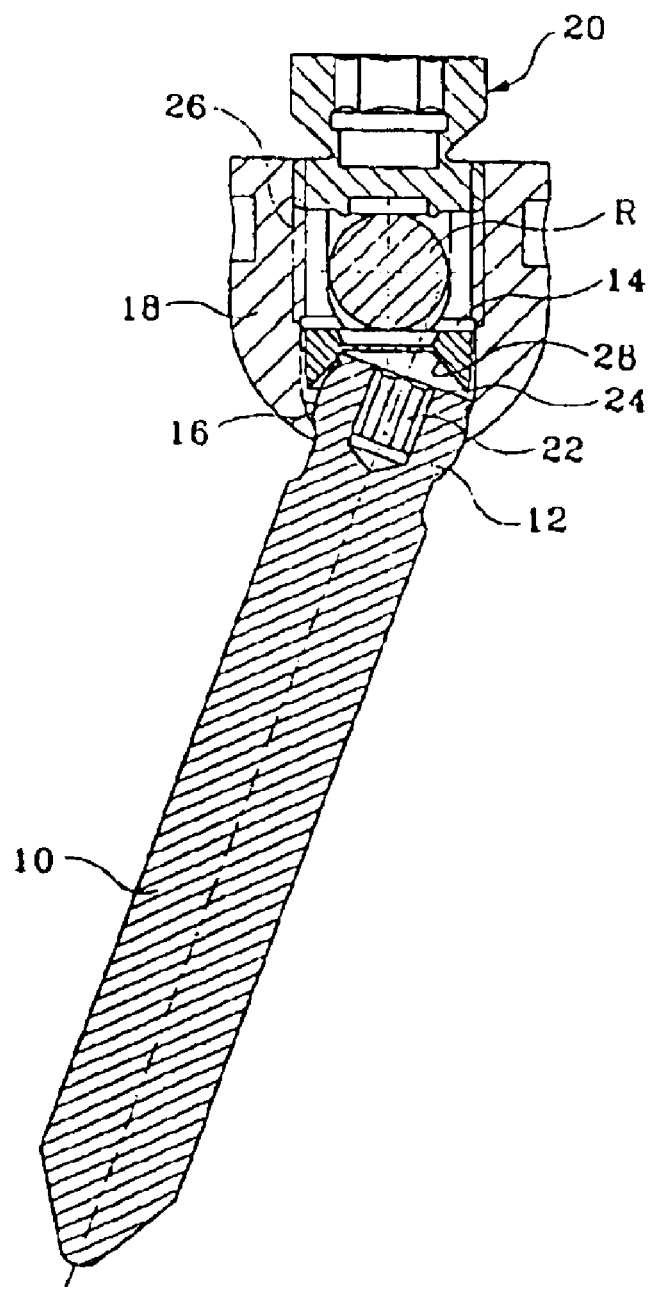
FIG. 1 is a cross-sectional view illustrating a conventional bone fixation apparatus.
Figure 2:
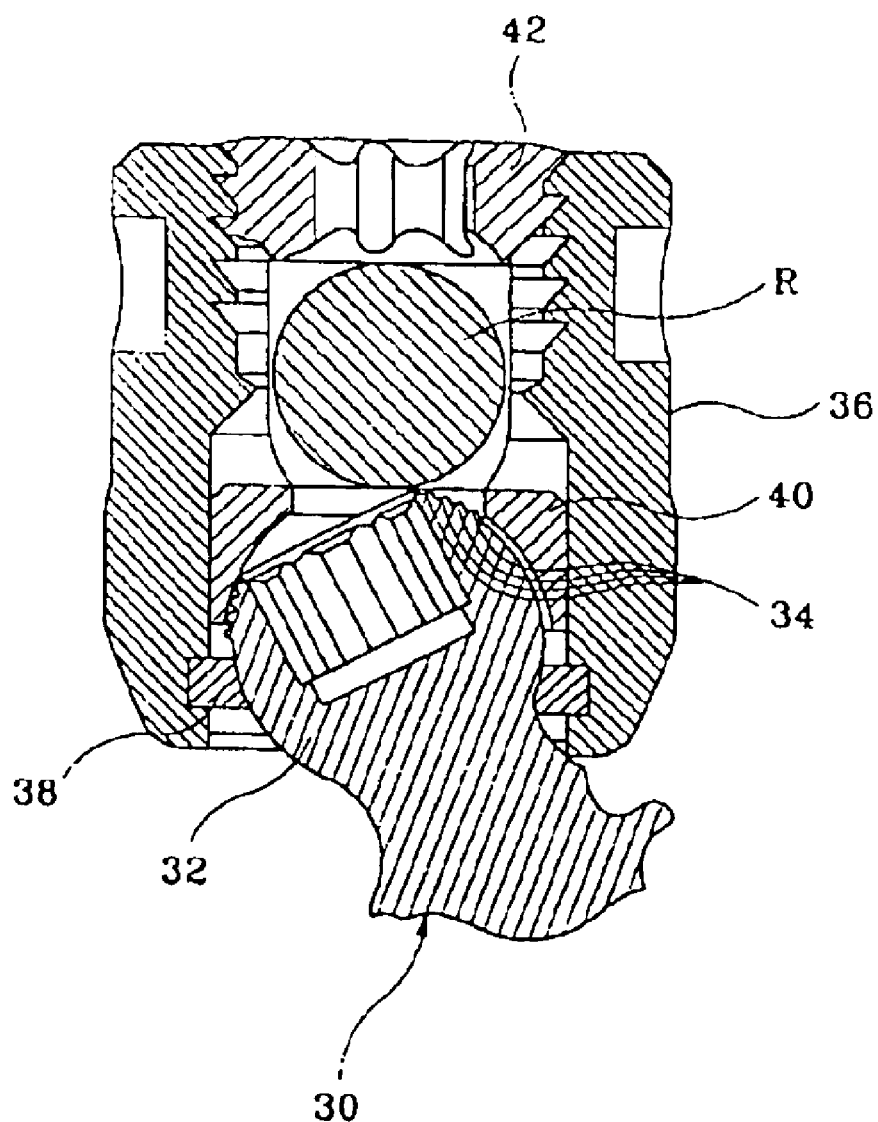
FIG. 2 is a cross-sectional view illustrating another conventional bone fixation apparatus.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 3:
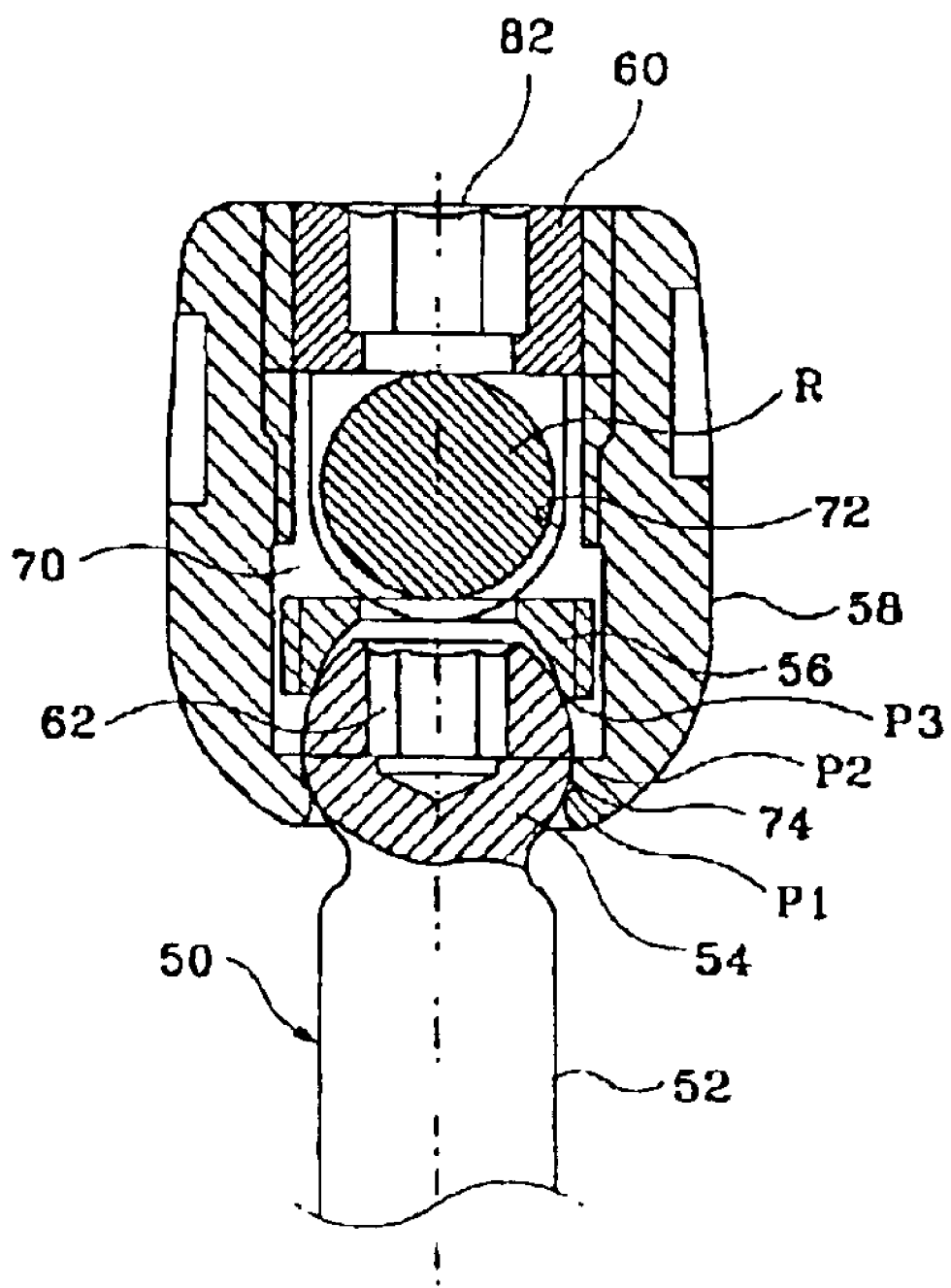
FIG. 3 is a cross-sectional view illustrating a bone fixation apparatus in accordance with an embodiment of the present invention.
Figure 4:
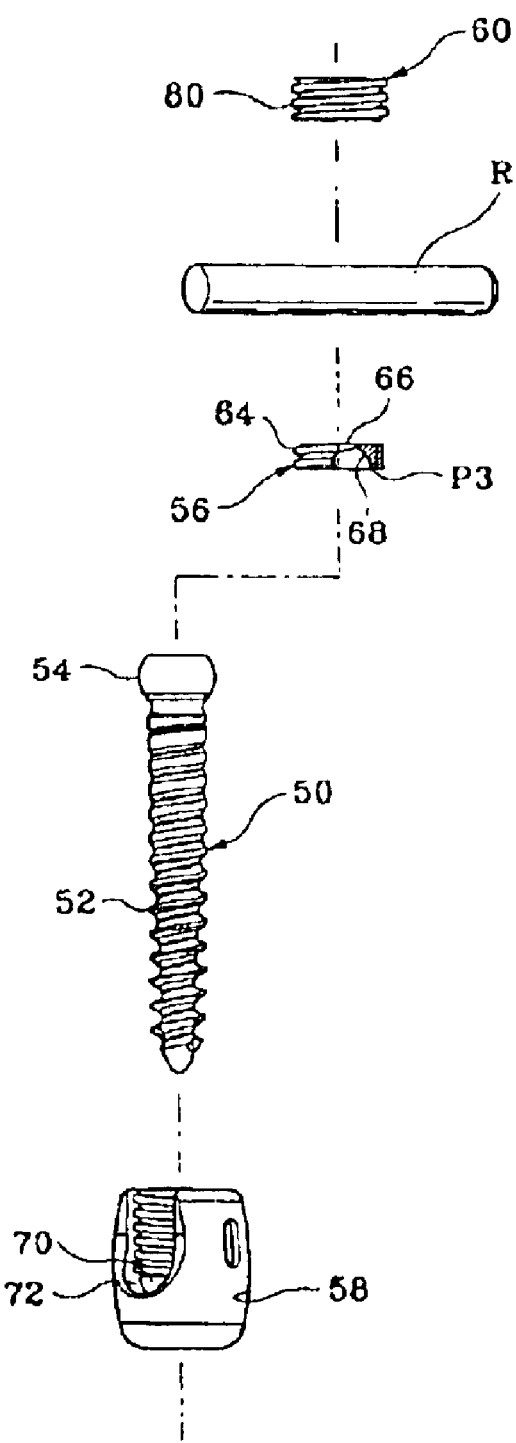
FIG. 4 is an exploded perspective view illustrating the bone fixation apparatus according to the present invention.

As shown in FIGS. 3 and 4, a bone fixation apparatus in accordance with an embodiment of the present invention includes a bone screw 50 which has external threads 52 and a head 54. An upper part of the head 54 of the bone screw 52 is supported by a cap member 56. The bone fixation apparatus further includes a receiver member 58 in which the head 54, the cap member 56 and a support bar R are accommodated and fixedly held. A compression member 60 for fixing the support bar R is threadedly coupled into an upper part of the receiver member 58.

The external threads 52 of the bone screw 50 are screwed into a bone. The lower end of the external threads 52 is pointed to be easily screwed into the bone. Although the root diameter of the external threads 52 is gradually decreased toward the lower end, the same crest diameter of the external threads 52 is maintained. If external threads of a bone screw have the same outer diameter and the same thread height throughout the entire length of the bone screw, a problem is caused in that, the bone screw is apt to shake because the fixing force is gradually decreased due to repetitive application of external force, etc. In an effort to cope with this problem, while a structure is disclosed in the art in which an outer diameter is gradually decreased toward the lower end of the bone screw, this structure encounters a drawback in that, due to the reduction in strength, the bone screw is likely to be broken. In consideration of this problem and drawback, in the present invention, the root diameter of the external threads is gradually decreased toward the lower end of the bone screw and the external threads have the same crest diameter. As a consequence, not only are the external threads securely fixed with respect to the bone, it is also possible to prevent the strength of the bone screw from being reduced.

The head 54 of the bone screw 50 has a truncated sphere-shaped configuration. A hexagonal groove 62 of a certain depth is defined on a flat upper end surface of the head 54 so that a tool such as a wrench and the like can be inserted into the hexagonal groove 62 to screw the bone screw 50 into the bone. It is to be noted that the head may have a groove of various sectional shapes.

Figure 6:
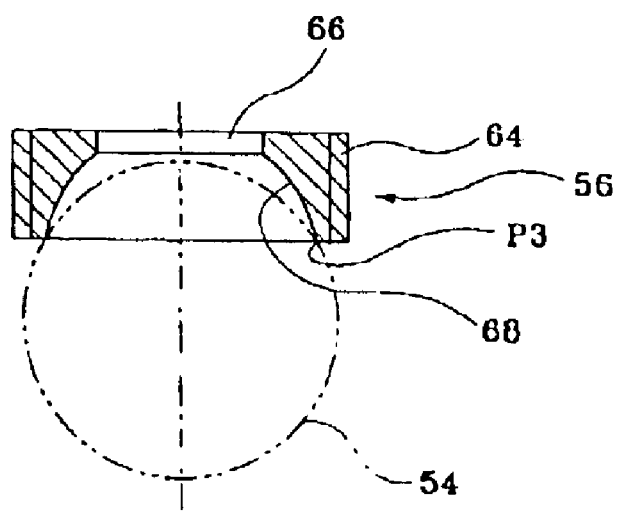
FIG. 6 is a cross-sectional view illustrating the cap member of FIG. 3.

As can be readily seen from FIG. 6, the cap member 56 has a disk-shaped configuration with threads 64 formed on a circumferential outer surface thereof. A hole 66 is defined through a center portion of the cap member 56 to communicate with the hexagonal groove 62. A recess 68 of a certain depth is defined on a lower surface of the cap member 56. The recess 68 possesses a rounded surface which has a radius of a curvature less than that of the head 54. At a lower end P3 of the recess 68, the cap member 56 is brought into linear contact with an outer surface of the upper part of the head 54. It is to be noted that the recess 68 may have a truncated cone-shaped contour. The threads 64 comprise trapezoidal threads in the same manner as the internal threads formed on the inner surface of the receiver member 58 which defines a bore.

Figure 5:
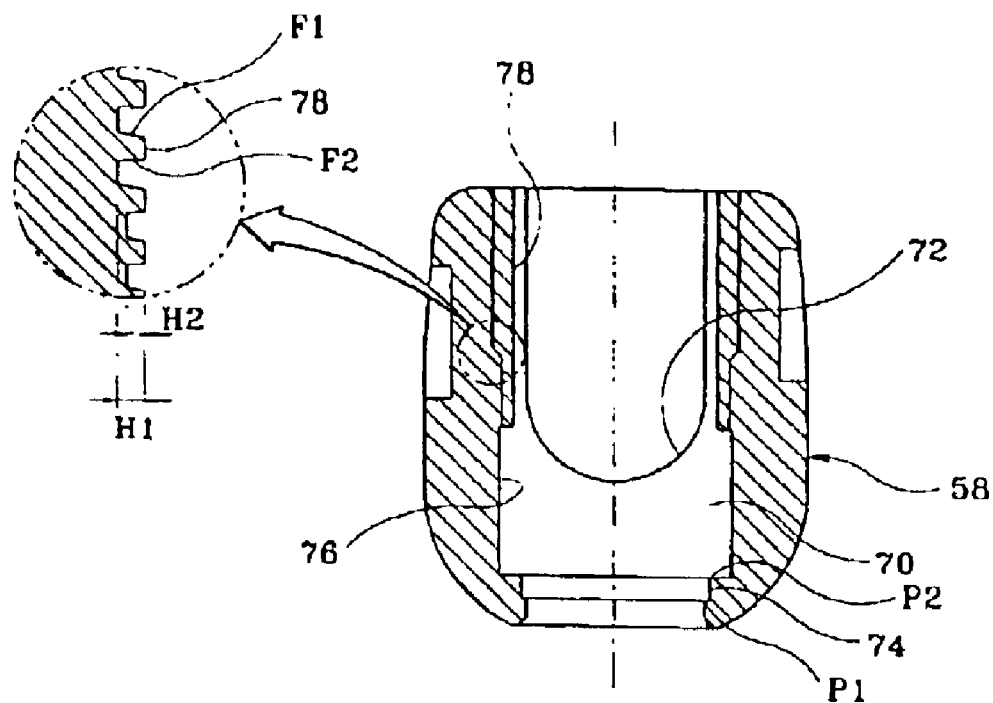
FIG. 5 is a cross-sectional view illustrating the receiver member of FIG. 3.

As shown in FIG. 5, the receiver member 58 has the bore 70 which extends in an axial direction and in which the cap member 56 and the head 54 of the bone screw 50 are respectively accommodated and fixedly held. The receiver member 58 further has a U-shaped channel 72 through which the support bar R extends.

Two stepped portions 74 are formed at a lower end and inner surface of the receiver member 58 to increase the supporting force for the head 54. Edges P1 and P2 of the stepped portions 74 are brought into linear contact with an outer surface of a lower part of the head 54. It is to be readily understood that three or four stepped portions 74 may be formed in place of the two stepped portions 74. The upper edge P2 of an upper stepped portion 74 has an inner diameter greater than that of the lower edge P1 of the lower stepped portion 74, in which the edges P1 and P2 of the stepped portions 74 can be brought into linear contact with the outer surface of the lower part of the spherical head 54.

The bore 70 is formed therein with stepped portions 74, an accommodating chamber 76 defined above the stepped portions 74 to accommodate the cap member 56, and internal threads 78 on which the cap member 56 is threadedly moved and to which the compression member 60 is threadedly coupled.

The accommodating chamber 76 has an inner diameter greater than that of the internal threads 78. Accordingly, the cap member 56 which is inserted into the accommodating chamber 76 after moving on the internal threads 78 is prevented from being unintentionally and upwardly released from the receiver member 58.

The upper portion of the internal threads 78 has a thread height H1 greater than that of the thread height H2 of the lower portion of the internal threads 78, so that the cap member 56 can be threadedly moved on both of the upper and lower portions of the internal threads 78 but the compression member 60 can be threadedly moved only on the upper portion and cannot be threadedly moved on the lower portion of the internal threads 78. The upper and lower portions of the internal threads 78 have the same thread pitch. Therefore, the compression member 60 is screwed only up to such a depth to downwardly bias the support bar R. In this regard, due to the fact that the compression member 60 can be positioned in a proper place even when the support bar R is not inserted through the U-shaped channel 72, assembly of the bone fixation apparatus can easily be performed within a short period of time.

The internal threads 78 comprise trapezoidal threads, so that deformation of the receiver member 58 can be prevented and the internal threads 78 can provide optimized results in terms of force transfer, locking efficiency, and likelihood of unscrewing. In this regard, in the case of a triangular thread, as the compression member 60 is screwed, while excellent locking force can be obtained, an axial force transfer rate becomes low. Also, because the receiver member 56 gets wider in a radial direction after locking of the compression member 60, a disadvantage is caused in that a separate cap member must be coupled to the receiver member 58. Further, a square thread suffers from defects in that, while an excellent axial force transfer rate is obtained, the likelihood of unscrewing is increased. In the present invention, due to the fact that trapezoidal threads are adopted, optimized results are provided in terms of force transfer and locking efficiency, and it is not necessary to couple a separate cap member to the receiver member.

It is preferred that the trapezoidal thread has an upper surface which is formed to have a slope F1 greater than the slope F2 of a lower surface. Thus, the cap member 56 and the compression member 60 can be easily assembled while preventing the cap member 56 from being unintentionally unscrewed. Concretely speaking, the upper and lower surfaces of the trapezoidal thread have slopes F1 and F2 of 10° and 1°, respectively. Since the upper slope is greater than the lower slope, the cap member 56 and the compression member 60 can be easily screwed downward. Also, deformation is minimized even when a force is upwardly applied. Moreover, as engagement between the internal threads 78 and the compression member 60 is maximized, precision is improved and unintentional unscrewing of the compression member 60 is avoided.

The compression member 60 has a cylinder-shaped configuration with threads 80 formed on a circumferential outer surface thereof. The threads 80 are threadedly coupled to the internal threads 78 of the receiver member 58. A hexagonal groove 82 and a hole 84 which communicate with each other are defined at a center portion of the compression member 60.

Hereafter, the assembly procedure of the bone fixation apparatus according to the present invention, constructed as mentioned above, will be described.

First, in a state wherein the bone screw 50 is positioned above the receiver member 58, the bone screw 50 is inserted downward into the bore 70 of the receiver member 58, in a manner such that the head 54 is seated on the multiple stepped portions 74. Then, the cap member 56 is moved downward through the internal threads 78 to be positioned in the accommodating chamber 76. At this time, in order to prevent the cap member 56 accommodated in the accommodating chamber 76 from being unintentionally and upwardly released from the receiver member 58, a punching process may be implemented in such a way as to leave a scar on the upper surface of the cap member 56.

Next, after inserting a wrench through the hole 66 of the cap member 56 into the hexagonal groove 62 of the head 54, the bone screw 50 is driven into the bone. Thereupon, the support bar R is inserted through the U-shaped channel 72 to be placed over the cap member 56, and the compression member 60 is screwed into the receiver member 58 so as to fix the bone screw 50.

The locking force of the compression member 60 is transferred through the support bar R and the cap member 56 to the head 54. At this time, due to the fact that the edges P1 and P2 of the stepped portions 74 of the receiver member 58 are brought into linear contact with the outer surface of the lower part of the head 54 and, at the lower end P3 of the recess 68, the cap member 56 is brought into linear contact with the outer surface of the upper part of the head 54. The bone screw 50 is securely fixed to prevent movement.

Figure 7:
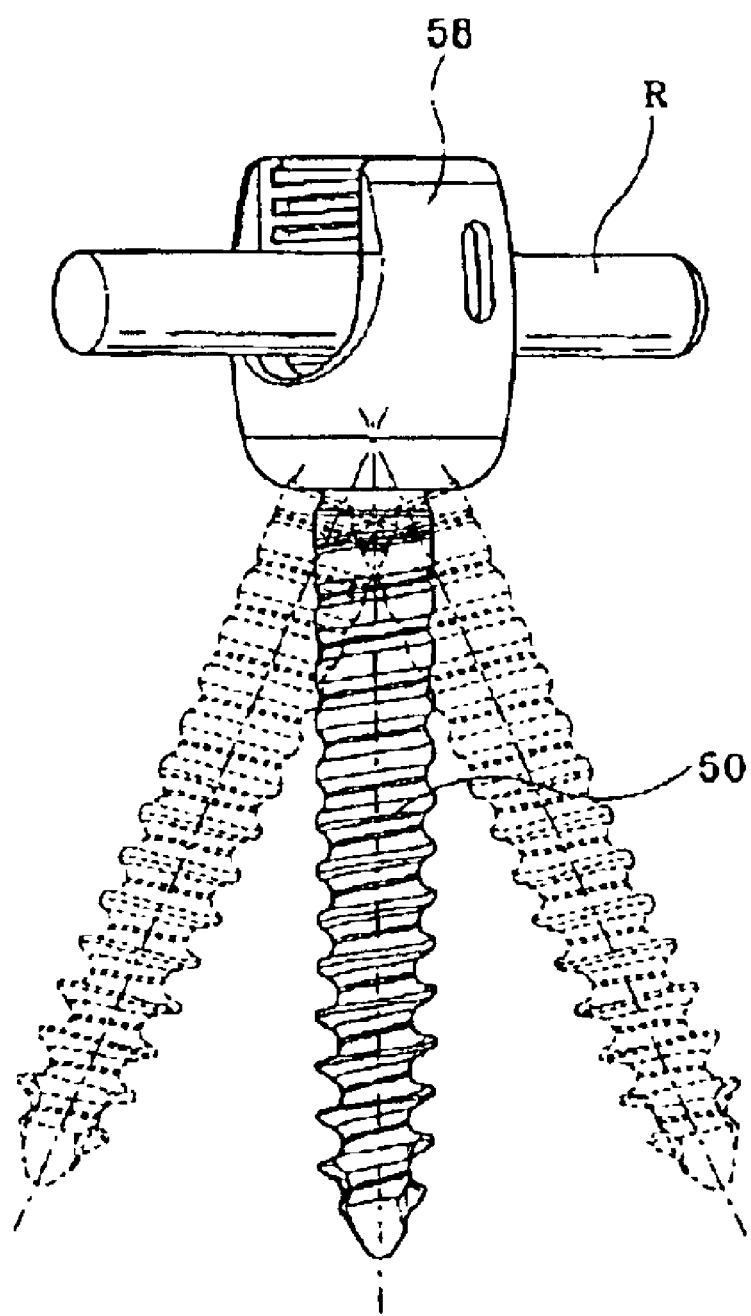
FIG. 7 is a perspective view illustrating the in-use status of the bone fixation apparatus according to the present invention.

As shown in FIG. 7, the bone screw 50 can be fixed in a state wherein it is inclined within 26° when measured from a center axis.

Figure 8:
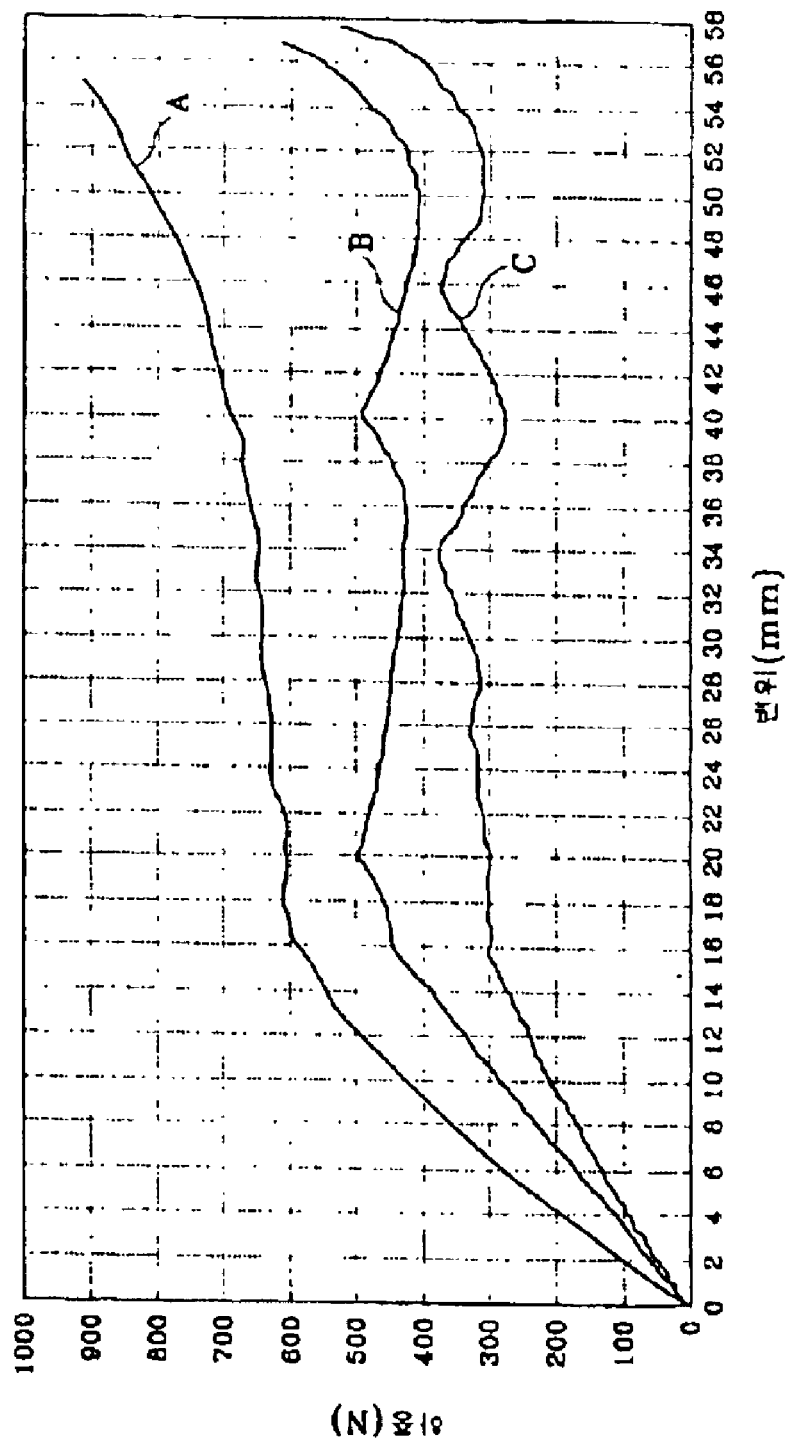
FIG. 8 is a graph reflecting the results of tests conducted with respect to the present bone fixation apparatus and the conventional bone fixation apparatuses.

FIG. 8 is a graph obtained by testing the present bone fixation apparatus and the conventional bone fixation apparatuses in terms of the supporting force of the bone screws. In each test, a compression member is screwed into a receiver member with a locking torque of 14 Nm, and a displacement is measured when a head yielded under static load application.

A universal compression tester having Model No. MTS 793 was used as a test equipment, and each test was implemented in accordance with ASTM F1717.

Figure 9:
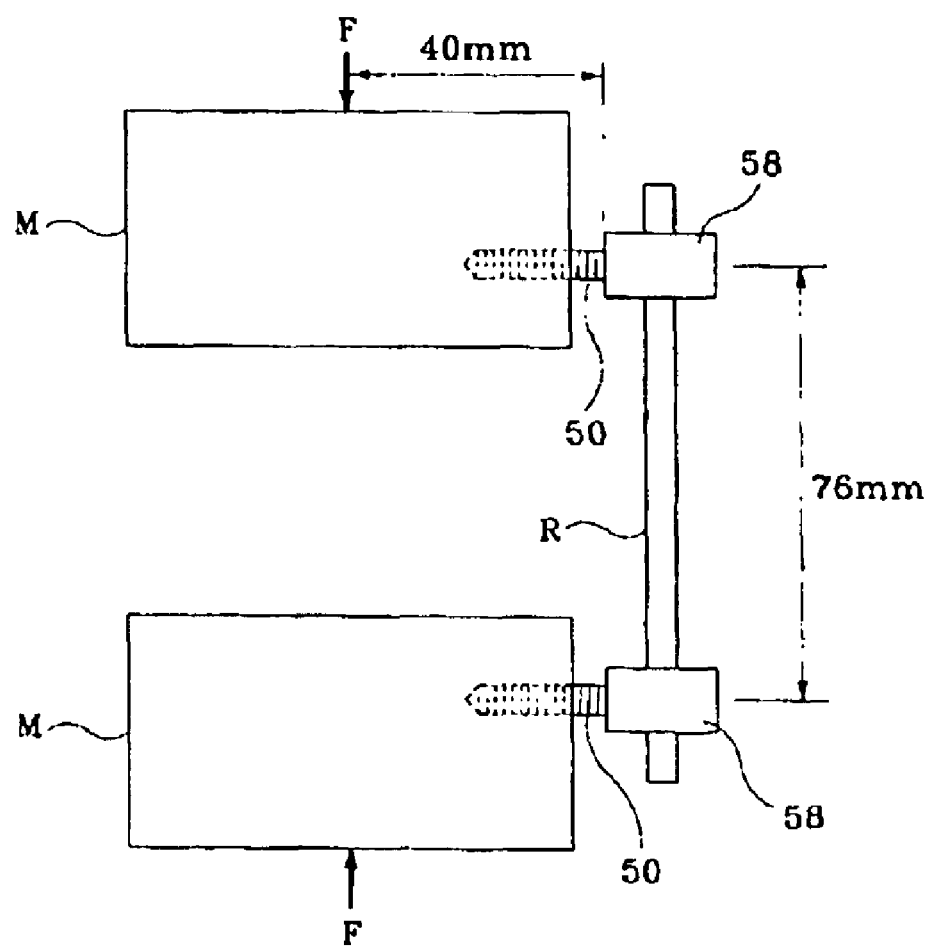
FIG. 9 is a schematic view for explaining a condition under which each bone fixation apparatus is tested.

FIG. 9 is a schematic view for explaining a condition under which each bone fixation apparatus is tested. As shown in FIG. 9, bone screws 50 are driven into upper and lower objects M to have a spacing of 76 mm. Thereafter, the support bar R is inserted through the receiver members 58 of the bone screws 50, and compression members (not shown) are screwed into the receiver members 58. Then, by applying a load F to each bone screw at a location separated by 40 mm from a head of each bone screw, deformation of the corresponding object was observed to produce the graph as depicted in FIG. 8.

In the graph, curve A represents the bone fixation apparatus manufactured according to the present invention, curve B represents the conventional bone fixation apparatus manufactured according to U.S. Pat. No. 6,280,442, and curve C represents the conventional bone fixation apparatus manufactured according to Korean Patent Laid-open Publication No. 2000-48562.

As can be readily seen from the graph, while the bone fixation apparatus according to the present invention has a yielding point of 550 N, the conventional bone fixation apparatuses respectively have yielding points of 450 N and 300 N. Therefore, it is to be readily understood that the bone fixation apparatus according to the present invention provides increased supporting force.

As apparent from the above description, the bone fixation apparatus according to the present invention provides advantages in that the supporting force of a bone screw is increased to prevent movement of a bone and assemblability of the bone fixation apparatus is improved. Further, in the bone fixation apparatus according to the present invention, the force transmission rate is increased, and unintentional unscrewing of a compression member is avoided.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A bone fixation apparatus comprising:
   a bone screw having a head;
   a cap member placed on an upper part of the head of said bone screw;
   a receiver member having a bore in which said cap member and the head of said bone screw are respectively accommodated and held, and a U-shaped channel through which a support bar extends;
   a compression member threadedly coupled into said receiver member to downwardly bias said support bar; and
   a plurality of distinct stepped portions formed at a lower end and inner surface of said receiver member, wherein the stepped portions are arranged to be brought into contact with an outer surface of a lower part of the head.

2. The bone fixation apparatus as set forth in claim 1, wherein a recess of a certain depth is defined on a lower surface of said cap member, and at a lower end of said recess, said cap member is brought into contact with an outer surface of the upper part of the head.

3. The bone fixation apparatus as set forth in claim 1, further comprising an accommodating chamber disposed within the bore of the receiver above the stepped portions, said accommodating chamber including a first portion and a second portion, said first portion including internal threads on which said cap member is threadedly moved and to which said compression member is threadedly coupled, said second portion including an inner diameter greater than an inner diameter of said first portion.

4. The bone fixation apparatus as set forth in claim 3, wherein an upper portion of the internal threads has a thread height greater than that of a lower portion of the internal threads, wherein said cap member includes threads sized and arranged such that said cap member can be threadedly moved on both the upper portion and lower portion of the internal threads, and wherein said compression member includes threads sized and arranged such that said compression member can be threadedly moved only on the upper portion and cannot be threadedly moved on the lower portion of the internal threads.

5. The bone fixation apparatus as set forth in claim 3, wherein the internal threads comprise trapezoidal threads, so that deformation of said receiver member can be prevented and the internal threads can provide optimized results in terms of force transfer, locking efficiency, and prevention of unscrewing.

6. The bone fixation apparatus as set forth in claim 5, wherein the trapezoidal threads have upper surfaces and lower surfaces, wherein said upper have slopes greater than that of said lower surfaces, so that said cap member and said compression member can be easily assembled while preventing said cap member from being unintentionally unscrewed.

7. The bone fixation apparatus as set forth in claim 6, wherein said upper and said lower surfaces of the trapezoidal threads have slopes of 10° and 1°, respectively.

* * * * *